(12) United States Patent
Ferrera (10) Patent No.: US 10,440,947 B2
(45) Date of Patent: Oct. 15, 2019

(54) AQUEOUS SOLUTION FOR PRESERVING AN ORGAN AND USES DURING HYPOTHERMIC ISCHEMIA

(71) Applicants: UNIVERSITE CLAUDE BERNARD LYON I, Villeurbanne (FR); INSERM (INSTITUT NATIONAL DE LA SANTE ET DE LA RECHERCHE MEDICALE), Paris (FR)

(72) Inventor: Rene Ferrera, Decines (FR)

(73) Assignees: INSERM (INSTITUT NATIONAL DE LA SANTE ET DE LA RECHERCHE MEDICALE), Paris (FR); UNIVERSITE CLAUDE BERNARD LYON I, Villeurbanne (FR)

( * ) Notice: Subject to any disclaimer, the term of this patent is extended or adjusted under 35 U.S.C. 154(b) by 74 days.

(21) Appl. No.: 15/036,432

(22) PCT Filed: Nov. 13, 2014

(86) PCT No.: PCT/FR2014/052897
§ 371 (c)(1),
(2) Date: May 13, 2016

(87) PCT Pub. No.: WO2015/071602
PCT Pub. Date: May 21, 2015

(65) Prior Publication Data
US 2016/0295855 A1  Oct. 13, 2016

(30) Foreign Application Priority Data
Nov. 15, 2013 (FR) ...................... 13 61227

(51) Int. Cl.
*A01N 1/02* (2006.01)
*A61K 38/15* (2006.01)
*A61K 51/04* (2006.01)

(52) U.S. Cl.
CPC .................. *A01N 1/0226* (2013.01)

(58) Field of Classification Search
None
See application file for complete search history.

(56) References Cited

U.S. PATENT DOCUMENTS

| 2009/0017439 A1* | 1/2009 | Shimko | A01N 1/02 435/1.1 |
| 2009/0048275 A1* | 2/2009 | Beauchamps | C07D 487/04 514/263.23 |
| 2012/0177615 A1* | 7/2012 | Cook | A01N 1/021 424/93.7 |

FOREIGN PATENT DOCUMENTS

| EP | 0 806 140 A1 | 11/1997 |
| WO | 01/20982 A2 | 3/2001 |
| WO | 02/41696 A1 | 5/2002 |
| WO | 2011/077024 A1 | 6/2011 |

OTHER PUBLICATIONS

International Search Report dated Feb. 9, 2015 for Application No. PCT/FR2014/052897.
Masters, T.N., et al., "Extending Myocardial Viability During Heart Preservation with Cyclosporine A", Journal of Heart and Lung Transplantation, vol. 19, No. 1, Jan. 1, 2000, p. 41, XP009002149, ISSN: 1053-2498, abstract.
Masters, T.N., et al., "Extending Myocardial Viability During Heart Preservation with Cyclosporine A", J. Card. Sur. Nov.-Dec. 2000, 15(6), 392-402.
Rajesh, K.G., et al., "Mitochondrial Permeability Transition-pore Inhibition Enhances Functional Recovery After Long-time Hypothermic Heart Preservation", Transplantation 2003, 15, 76(9), 1314-1320.
Oka, N., et al., "Inhibition of mitochondrial remodeling by cyclosporine A preserves myocardial performance in a neonatal rabbit model of cardioplegic arrest", J. Thorac. Cardiovasc. Surg. Mar. 2008, 135(3), 585-593.
Gemici, G, et al., "Paclitaxel-induced ST-Segment Elevations", Clinical Cardiology, vol. 32, Issue 6, pp. E94-E96, 2009.
Cabani, E, et al., "Late myocardial ischemia with ST-segment elevation after negative dobutamine stress echocardiography in a patient with normal coronary arteries", J. Cardiovasc. Med. (Hagerstown), Apr. 2009, 10(4), 336-339.
Schrader, C., et al., "Symptoms and Signs of an Acute Myocardial Ischemia Caused by Chemotherapy with Paclitaxel (TAXOL) in a Patient with Metastatic Ovarian Carcinoma", Eur. J. Med. Res. Nov. 16, 2005, 10(11), 498-501.
Evtodienko, Y.V., et al., "Microtubule-active drugs suppress the closure of the permeability transition pore in tumour mitochondria", FEBS Lett. Sep. 9, 1996, 393(1), 86-88.

(Continued)

*Primary Examiner* — Renee Claytor
*Assistant Examiner* — Sharon M. Papciak
(74) *Attorney, Agent, or Firm* — Ladas & Parry LLP; Malcolm J. MacDonald (57) ABSTRACT

The present invention relates to an aqueous solution for organ preservation, in particular for the myocardium, the solution comprising:

100 mM to 130 mM of $Na^+$;
12 mM to 15 mM of $K^+$;
0.25 mM to 1.3 mM of $Ca^{++}$;
0.5 µM to 1.5 µM of cyclosporin A; and
0.5 µM to 1.5 µM of taxol, and it also relates to the joint use of cyclosporin A and taxol in a solution for in vitro preservation of an organ, in particular the myocardium.

17 Claims, 3 Drawing Sheets

(56) References Cited

OTHER PUBLICATIONS

Kidd, J.F., et al., "Paclitaxel Affects Cytosolic Calcium Signals by Opening the Mitochondrial Permeability Transition Pore", J. Biol. Chem. Feb. 22, 2002, 227(8), 6504-6510.

Mironov, S.L., "[Ca2+]i Signaling between Mitochondria and Endoplasmic Reticulum in Neurons Is Regulated by Microtubules", J. Biol. Chem. Jan. 7, 2005, 280(1), 715-721.

Hosgood, S.A., "The Role of Perfluorocarbon in Organ Preservation", Transplantation, May 27, 2010 89(10), 1169-1175.

Aldakkak, M., et al., "Adding ROS Quenchers to Cold $K^+$ Cardioplegia Reduces Superoxide Emission During 2-Hour Global Cold Cardiac Ischemia", J. Cardiovasc. Pharmacol. Ther. Mar. 2012, 17(1), 93-101.

Watson, A.J., et al., "Enhanced preservation of the rat heart after prolonged hypothermic ischemia with erythropoietin-supplemented Celsior solution", J. Heart Lung Transplant, Jun. 2013, 32(6), 633-640.

Oriyanhan, W., et al., "Taurine prevents myocardial ischemia/reperfusion-induced oxidative stress and apoptosis in prolonged hypothermic rat heart preservation", Heart Vessels, Nov. 2005, 20(6), 278-285.

Ozcinar, E., et al., "Improvement of Functional Recovery of Donor Heart Following Cold Static Storage with Doxycycline Cardioplegia", Cardiovasc. Toxicol. Oct. 9, 2013, 64-73.

Zheng, X, et al., "Novel Small Interfering RNA—Containing Solution Protecting Donor Organs in Heart Transplantation", Circulation, Sep. 22, 2009, 120(12), 1099-1107.

Michel, P, et al., "A Comparative Study of the Most Widely Used Solutions for Cardiac Graft Preservation During Hypothermia", J. Heart. Lung Transplant, 2002, 21, 1030-1039.

Ferrera, R., et al.,"Amélioration de la préservation des greffons cardiaques avant transplantation", Bull. Acad. Natle. Med., 2011, 195, Nos. 4 and 5, session of May 31, 2011, pp. 861-881.

\* cited by examiner

AQUEOUS SOLUTION FOR PRESERVING AN ORGAN AND USES DURING HYPOTHERMIC ISCHEMIA

This application is a 371 of PCT/FR2014/052897 filed on Nov. 13, 2014, which claims priority to French application number 1361227, filed on Nov. 15, 2013.

The present invention relates to the technical field of solutions for preserving organs. More precisely, the invention relates to aqueous solutions for preserving an organ during hypothermic ischemia, and preferably for preserving the myocardium, the solutions including cyclosporin A and taxol, and it also relates to uses thereof.

Some solutes (fewer than a dozen) do indeed exist that are used in clinical practice for preserving cardiac grafts. Nevertheless, the length of time a cardiac graft can be preserved before being transplanted is presently limited to the range 4 hours (h) to 6 h, which is rather short.

It is therefore desirable to propose solutions that enable preservation times to be improved, while still ensuring that the organ is viable.

Hundreds of molecules are potentially cardioprotective during an infarction (a warm ischemia of the heart situation). Some such molecules, such as cyclosporin A (J. Card. Sur. 2000, November-December, 15(6) 392-402; Transplantation 2003, 15, 76(9), 1314-20; and J. Thorac. Cardiovasc. Surg. 2008 March 135(3), 585-93) have even been found to be effective during the hypothermic stop stage (a cold ischemia of the cardiac graft situation). The action of taxol on the mitochondrial transition pore is controversial (Clinical Cardiology, Vol. 32, Issue 6, pages E94-E96; Ann. Pharmacother, 1996 October, 30(10), 1110-2; J. Cardiovasc. Med. (Hagerstown), 2009 April, 10(4), 336-9; Eur. J. Med. Res. 2005, Nov. 16, 10(11), 498-501; FEBS Lett. 1996 Sep. 9, 393(1), 86-8; J. Biol. Chem. 2002, Feb. 22, 227(8), 6504-10; and J. Biol. Chem. 2005, Jan. 7, 280(1), 715-21).

Other molecules have also been evaluated for protecting a graft during cold ischemia, such as perfluorocarbons (Transplantation, 2010 May 27; 89(10): 1169-75), anti-radical agents (J. Cardiovasc. Pharmacol. Ther. 2012 March; 17(1); 93-101), erythropoietin (EPO) (J. Heart Lung Transplant, 2013 June; 32(6); 633-40), taurine (*Heart Vessels*, 2005 November; 20(6): 278-85), or indeed inhibit Certain factors such as metalloproteinases MMP2 (*Cardiovasc Toxicol*. Cardiovasc. Toxicol. 2013 Oct. 9, Epub ahead of print) or TNFa by SiRNAs (Circulation, 2009 Sep. 22; 120(12): 1099-107).

As examples of solutions that have been proposed, mention may be made of the work by one of the inventors of the present patent application, and in particular of the solutions described in J. Heart. Lung Transplant, 2002, 21: 1030-1039, which describes a first generation of a solution known as LYPS. In the article published in Bull. Acad. Natle. Med., 2011, 195, Nos. 4 and 5, session of May 31, 2011, pages 861-881, it is emphasized that it is very difficult to undertake comparative studies of preservation media. A LYPS solution is mentioned together with eleven other solutions, some of which are in clinical use.

One of the objects of the invention is to propose a novel solution for preserving cardiac organs, in particular one that is suitable for hypothermic preservation. This solution should prolong the duration for which cardiac organs can be preserved, while ensuring viability and making subsequent transplantation possible.

In this context, the invention provides an aqueous solution for preserving the myocardium, the solution comprising:
100 mM to 130 mM of $Na^+$;
12 mM to 15 mM of $K^+$;
0.25 mM to 1.3 mM of $Ca^{++}$;
0.25 µM to 1.5 µM of cyclosporin A; and
0.25 µM to 1.5 µM of taxol.

Compositions of the invention preferably have 1±0.3 µM of taxol and 1±0.3 µM of cyclosporin A, and more preferably 1 µM of taxol and 1 µM of cyclosporin A.

The invention also provides the joint use of cyclosporin A and of taxol in a solution used for in vitro preservation of the myocardium, the joint use of cyclosporin A and of taxol in a solution used for in vitro hypothermic perfusion or immersion of the myocardium, and the joint use of cyclosporin A and of taxol in a solution used for hypothermic preservation of the myocardium, and in particular of a cardiac graft, in particular during cold ischemia, e.g. at a temperature from 4° C. to 15° C. The invention also provides associated preservation and perfusion methods.

In such uses and methods, the myocardium or cardiac graft may be immersed in the preservation solution containing the association of cyclosporin A and of taxol. It is possible to use the preservation solution as a cardioplegic solution, in particular for performing hypothermic perfusion of a cardiac organ, in particular as a physiological solution in a device of the kind described in application WO 2011/077024.

In such uses and methods, cyclosporin A and taxol are used jointly, in particular to ensure viability for the myocardium, and in particular for a cardiac graft, prior to transplanting. Their joint use makes it possible to improve the effect that is obtained on the viability of myocardium cells, in particular when they are placed in hypothermia and then subjected to reperfusion. The methods and uses described for the myocardium may be extended to any type of organ such as the kidney or the liver. When they are used as grafts, such organs are placed for long periods of time in a static hypothermic preservation situation at 4° C. (cold ischemia), during which it is necessary to prevent the tissue of the graft spoiling progressively. The association of the invention of cyclosporin A and of taxol, and in particular the preservation solutions described in the context of the invention, enable the cells of these various grafts to be protected from the suffering associated with such cold ischemia. Advantageously, in such uses and methods, the cyclosporin and the taxol are each present in the solution at a concentration of 1±0.5 µM, preferably at a concentration of 1±0.3 µM, and more preferably at a concentration of 1 µM. In preferred manner, cyclosporin and taxol are used in a solution as defined in the context of the invention.

The invention is described below in detail.

In the present description, concentrations are given relative to the total solution. mM is used to mean mmol/L. For insulin, IU corresponds to the international unit of activity.

In the preservation solutions of the invention, two agents are used for the first time in combination in the context of cardioprotection of a cardiac graft: they are Cyclosporin A (CAS number: 59865-13-3) and Taxol (also known as paclitaxel—CAS number: 33069-62-4). These two compounds act synergistically and they provide anti-ischemic action. Thus cyclosporin A (CsA) is for inhibiting mitochondrial pore transition permeability (MPTP), while taxol presents stabilizing action on cellular microtubules. Nevertheless, taxol also possesses undesired action that is the opposite of cyclosporin A (opening MPTP). The association of CsA and taxol envisaged in the context of the invention serves to retain the beneficial effect of taxol while limiting its deleterious effects on the heart.

The purpose of the solutions of the invention is to lengthen the time an organ can be preserved, preferably the myocardium and in particular cardiac grafts, while maintaining the viability of the organ in optimum manner.

In addition, the preservation solution of the invention presents the following characteristics:

It is a solution of extracellular type. It contains 100 mM to 130 mM of $Na^+$, and preferably 120±10 mM of $Na^+$. This sub-physiological concentration is intended to avoid intracellular sodium overload (resulting from the opening of potential-dependent sodium channels) and consequently avoids the resulting calcium overload.

Although it is of the extracellular type, the composition nevertheless has a moderately high level of potassium. It contains 12 mM to 15 mM of $K^+$, and preferably 13±1 mM of $K^+$. This non-physiological concentration of $K^+$ is both high enough to induce cardioplegia (stopping of the heart) by depolarizing cardiomyocytes, and sufficiently low to protect the vascular endothelium, which is very sensitive to high values of $K^+$.

It is a low calcium solution. It contains 0.25 mM to 1.3 mM of $Ca^{++}$, and preferably 1±0.3 mM of $Ca^{++}$. This concentration of calcium is to avoid calcium overload, which is extremely prejudicial for the heart.

The presence of these various ions, at the above-recommended concentrations, makes it possible simultaneously to stop the heart (cardioplegia) and to protect it against calcium invasion.

Advantageously, in the solutions of the invention, low calcium is associated with one or indeed two compounds for regulating exchanges of calcium, so as to further improve protection against calcium invasion:

magnesium $Mg^{++}$, a competitor of $Ca^{++}$, preferably present in the composition at 3.5 mM to 13 mM, and more preferably at 4±0.5 mM; and/or procaine, a sodium channel inhibitor, and consequently an inhibitor of calcium entering the cell via the Na/Ca exchanger, is preferably present in the composition at 1±0.5 mM. Furthermore, the entry of $Na^+$, can be deleterious for a cell in hypothermia since it induces edema. Since procaine inhibits this entry of $Na^+$ into cells, it provides protection against edemas.

Advantageously, preservation solutions of the invention contain polyethylene glycol (PEG), and in particular two different types of PEG: PEG having a mean molecular weight of 8000 Da±10% is used for its vascular osmotic activity, and PEG having a mean molecular weight of 20,000 Da±10% is used for its anti-inflammatory role and its role of immuno-masking antigen sites. The use of these two PEGs makes it possible to combat edema more effectively. In conventional manner, the molecular weight of PEGs can be determined using the method of chromatographic permeation on gel.

In particular, the solution of the invention comprises:
polyethylene glycol having a mean molecular weight of 8000 daltons±10%, at 2±0.5 g/L; and
polyethylene glycol having a mean molecular weight of 20,000 daltons±10%, at 3±0.5 g/L.

It is also desirable for the preservation solutions of the invention to contain metabolic substrates and/or activators:

glucose associated with insulin for stimulating anaerobic glycolysis: insulin stimulates the entry and the use of glucose in the cell; and/or pyruvate associated with insulin for activating aerobic glycolysis: insulin stimulates the use of pyruvate in mitochondria in order to produce energy. Pyruvate has an anti-radical function; and/or glutamate associated with aspartate for stimulating the Krebs cycle: aspartate and glutamate are two amino acids that, in combination and in the presence of pyruvate, are capable of being used by mitochondria in the absence of oxygen to produce energy.

These various compounds act synergistically and enable the metabolism of cardiac cells to be activated in spite of deep hypothermia, e.g. at 4° C., and in particular they enable the Krebs cycle to be activated and consequently they enable mitochondrial oxidative phosphorylation.

Advantageously, the preservation solution of the invention also includes:

either 250±10 IU/L of insulin and 20±1 mM of glucose;

or 250±10 IU/L of insulin and 2.5±0.1 mM of pyruvate;

or 250±10 IU/L of insulin, 20±1 mM of glucose, and 2.5±0.1 mM of pyruvate;

or 2.5±0.1 mM of pyruvate, 2±1 mM of aspartate, and 1.4±1 mM of glutamate;

or 250±10 IU/L of insulin, 2.5±0.1 mM of pyruvate, 2±1 mM of aspartate, and 1.4±1 mM of glutamate;

or 250±10 IU/L of insulin, 20±1 mM of glucose, 2.5±0.1 mM of pyruvate, 2±1 mM of aspartate, and 1.4±1 mM of glutamate;

or 250±10 IU/L of insulin, 20±1 mM of glucose, 2.5±0.1 mM of pyruvate, 2±1 mM of aspartate, and 1.4±1 mM of glutamate.

In solutions of the invention, the ions $Na^+$, $K^+$, $Ca^{++}$, and $Mg^{++}$, when present, are generally introduced in the form of salts, in particular in the form of NaCl, KCl, $CaCl_2$, and $MgCl_2$, respectively, or else in the form of counter-ions of other introduced compounds of the aspartate, pyruvate, and glutamate type. Thus in general solutions of the invention include $Cl^-$ ions associated with the quantities of $Na^+$, $K^+$, $Ca^{++}$, and $Mg^{++}$ ions that are present.

Preservation solutions of the invention may optionally contain adenosine, preferably at 5±1 mM. Adenosine is a vasodilator and also an activator of the PKC signaling channel, known for its cardioprotective effects.

Preservation solutions of the invention may also further contain an anti-radical agent, such as reduced glutathion (CAS number 70-18-8), preferably at 5±1 mM.

Advantageously, the solutions of the invention have osmolarity and/or pH that are close to physiological values. Preferably, preservation solutions of the invention present osmolarity in the range 280 mOsm/L to 320 mOsm/L, and preferably about 290 mOsm/L. Preservation solutions of the invention are preferably buffered to a pH of 7.35±0.05. It is possible to use any type of appropriate buffer solution, such as a HEPES solution (4-(2-hydroxyethyl)-1-piperazine ethanesulfonic acid), histidine, or a phosphate solution.

As a particular example of compositions of a solution of the invention, mention may be made of compositions that comprise:

120±10 mM of $Na^+$;
13±1 mM of $K^+$;
1±0.3 mM of $Ca^{++}$;
1±0.5 μM of cyclosporin A;
1±0.5 μM of taxol;
4±0.5 mM of $Mg^{++}$;
130±12 mM of $Cl^-$;
2±0.5 g/L of polyethylene glycol having a mean molecular weight of 8000 daltons±10%;

3±1 g/L of polyethylene glycol having a mean molecular weight of 20,000 daltons±10%;
250±10 IU/L of insulin;
20±1 mM of glucose;
2.5±0.1 mM of pyruvate;
2±1 mM of aspartate;
1.4±1 mM of glutamate;
1±0.5 mM of procaine; and
and water.

It is also possible to add 5±1 mM of adenosine and/or 5±1 mM of reduced glutathione to this composition.

The solution may be buffered to a pH of 7.35±0.1 with a HEPES buffer.

As a more precise example of such a composition, mention may be made of a composition that comprises:
120 mM of $Na^+$;
13 mM of $K^+$;
1 mM of $Ca^{++}$;
1 µM of cyclosporin A;
1 µM of taxol;
4 mM of $Mg^{++}$;
130 mM of $Cl^-$;
2 g/L of polyethylene glycol having a mean molecular weight of 8000 daltons±10%;
3 g/L of polyethylene glycol having a mean molecular weight of 20,000 daltons±10%;
250 IU/L of insulin;
20 mM of glucose;
2.5 mM of pyruvate;
2 mM of aspartate;
1.4 mM of glutamate;
1 mM of procaine; and
and water.

The composition of such solutions is the result of making selections from among certain possible compounds, at a quasi-optimum concentration, in association with other compounds with which they interact, thus making it possible to act at different levels on protecting the heart in hypothermia, thereby imparting their particularly satisfactory effectiveness to said solutions.

It is also possible for preservation solutions of the invention to include a compound for increasing membrane fluidity, such as ethanol, preferably at 10±5 mM. Such a compound serves to increase the fluidity of cell membranes which tend to stiffen during hypothermia, thereby blocking ion pumps.

The examples below, described with reference to the accompanying figures, serve to illustrate the invention but have no limiting character.

EXAMPLES

The general objective of the following studies was to improve the survival of cardiac cells subjected to cold ischemia (4° C.), followed by normothermic reperfusion, a situation that is encountered by a cardiac graft prior to transplantation.

The combined use of Cyclosporin A and Taxol has been evaluated in order to reveal their synergistic action.

In this study, the models used were as follows:
cell culture of rat cardiomyocytes (in primary culture and in cell line); and
a perfused isolated rat heart in Langendorff mode.

1. Determining Optimum Concentrations
1.1. Equipment and Methods
1.1.1 Preparing Primary Cardiomycotes This was a conventional model for primary culture of cardiomyocytes. About 40 newborn rats were used for each experiment. The pups were decapitated and placed for 5 seconds (s) in a beaker containing alcohol at 70° C. The left ventricle of each heart was minutely extracted and then placed in an Erienmeyer containing cold PBS (GIBCO, pH 7.4) preserved in ice. Once all the hearts had been extracted, they were washed three times in PBS, and then transferred into a d35 Petri dish. They were then reduced into very fine fragments. The resulting fragments were washed again, three times. The fragments were placed in the trypsinator and trypsination (PB with 0.3% trypsin) was performed nine times for 10 minutes (min) at 37° C. After centrifuging (10 min at 1500 g), the supernatant was eliminated and the pellets were suspended in a growth medium at 37° C. In order to separate the cardiomyocytes (CM) and the cardiofibroblasts (CF), two differential attachments were performed (30 min and 120 min). The various cell types were returned to the growth medium with an additional 15% fetal bovine serum (FBS) (PAA®), counted on Mallassezia cells. The cells were then seeded at $2.5 \times 10^5$ cells per square centimeter ($cm^2$).

1.1.2 Preparing Cell Line Cardiomyocytes

This was a conventional model for culturing rat cardiomyocytes. The H9c2 cardiac cells (ATTC®) came from rat heart ventricles transfected with a pSV3 plasmid containing the SV40 gene. The cells were cultivated in high glucose Dulbecco's modified Eagle's medium (DMEM) (PAA®), with an additional 10% of Mycoplex FBS (PAA®) and 1% penicillin-streptomycin. The medium was changed every two days and re-seeding was performed at 70%-80% confluence.

1.1.3 MTT Viability Testing

MTT, or trimethyltetrazolium (Sigma), is a molecule that bonds to mitochondrial dehydrogenases (DH) in the presence of oxidized nicotimamide adenine dinucleotide and nicotimamide adenine dinucleotide phosphate (NAD+ and NADP+) coenzymes to form insoluble formazan crystals of violet color. The resulting violet color is evidence of mitochrondrial function and thus of cell viability. The crystals were dissolved in a permeabilization solution (dimethyl sulfoxide or DMSO, Sigma). This solubilization of formazan also gives rise to cell lysis. The plates were read by spectrophotometry (Multiskan Ex, Thermo, Electron Corporation®) at 550 nanometers (nm).

1.1.4 Cold ischemia—Reperfusion Procedure

The purpose of this protocol was to determine the potentially protective effect of cyclosporin and/or taxol on cardiomyocytes placed in a cold ischemia situation at 4° C. for 24 hours (h), followed by reperfusion for 24 h, at the end of which the viability test (the MTT test) was performed. A "sham" group was not subjected to the ischemia—reperfusion sequence. At each of the doses tested, four different experiments were performed, and during each experiment, eight different cell wells were tested simultaneously.

Statistical analysis consisted in comparing means (Student's test between the group under study and the control group).

1.2 Result. Rat Heart Cell Model in Primary Culture

Figure 1:
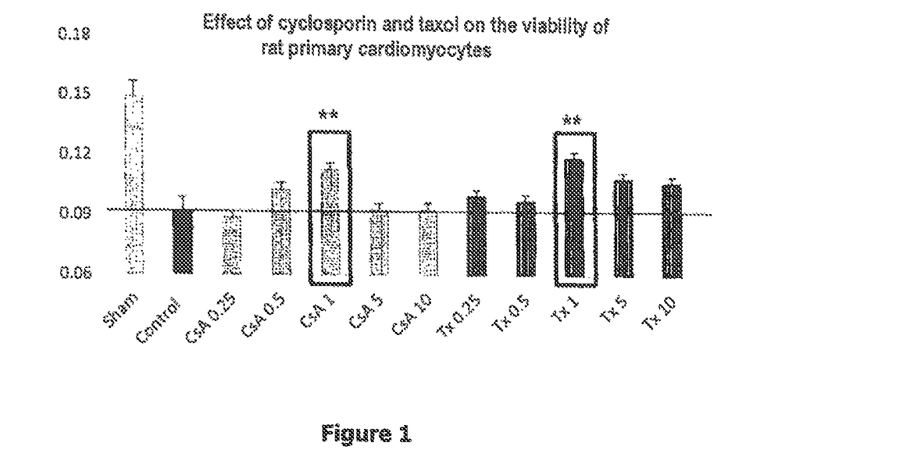
FIG. 1 shows the effect of cyclosporin and taxol on the viability of rat primary cardiomyocytes.

The viability of the primary cardiomyocytes was evaluated after 24 h of cold ischemia and 24 h of reperfusion. During the cold ischemia, the cells were maintained in various different media and the corresponding results are shown in FIG. 1:

In a St. Thomas basal solution (cardioplegic solution)="control" group. The horizontal black line thus corresponds to the base viability of cardiomyocytes in this standard cold ischemia—reperfusion condition.

In the same basal solution together with cyclosporin A (CsA) in order to obtain a final concentration in the medium of 0.252 μM (0.25 CsA group), or of 0.5 μM (0.5 CsA group), or of 1 μM (1 CsA group), or of 5 μM (5 CsA group), or of 10 μM (10 CsA group).

In the same basal solution together with taxol (Tx) in order to obtain a final concentration in the medium of 0.25 μm (0.25 Tx group), or of 0.5 μM (0.5 Tx group), or of 1 μM (1 Tx group), or of 5 μM (5 Tx group), or of 10 μM (10 Tx group).

The sham group was not subjected to the cold ischemia—reperfusion sequence.

The values correspond to means±SEM (n=32, performed as four different series of experiments over four weeks). **: $p<0.01$.

The data of FIG. 1 shows that:

At certain concentrations, both cyclosporin A and taxol can increase the viability of cardiac cells during a cold ischemia—reperfusion sequence.

For each of these two agents, there exists an optimum concentration around 1 μM (boxed results in FIG. 1), enabling cardiomyocyte viability to be increased by about 25% ($p<0.01$).

1.3 Result. Cell Model using H9c2 Cell Line Cardiac Cells

Figure 2:
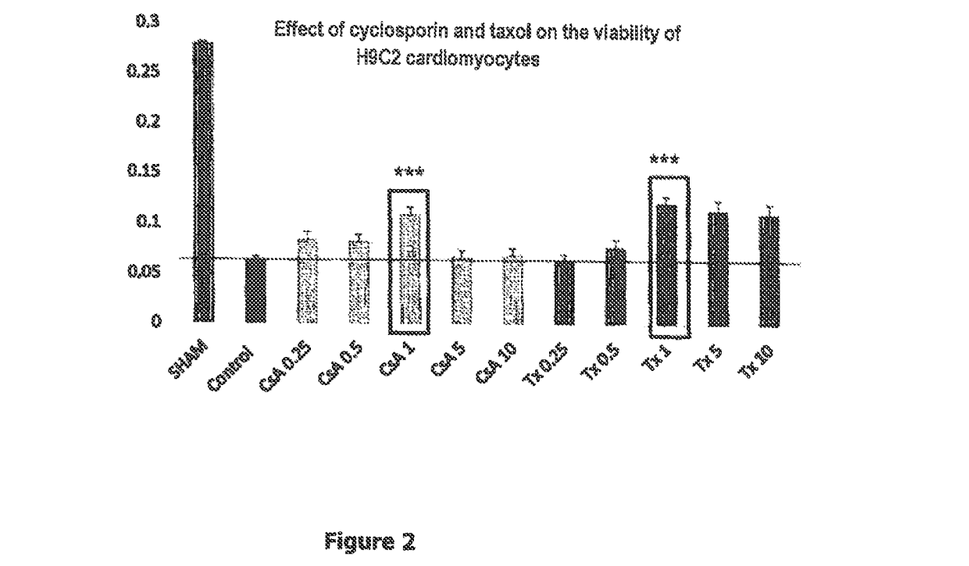
FIG. 2 shows the effect of cyclosporin and taxol on the viability of H9c2 cardiomyocytes.

The viability of primary cardiomyocytes was evaluated after 24 h of cold ischemia and 24 h of reperfusion. During the cold ischemia, the cells were maintained in different media and the corresponding results are shown in FIG. 2:

In a St. Thomas basal solution (cardioplegic solution)="control" group. The horizontal black line thus corresponds to the base viability of cardiomyocytes in this standard cold ischemia—reperfusion condition.

In the same basal solution together with cyclosporin A (CsA) in order to obtain a final concentration in the medium of 0.252 μM (0.25 CsA group), or of 0.5 μM (0.5 CsA group), or of 1 μM (1 CsA group), or of 5 μM (5 CsA group), or of 10 μM (10 CsA group).

In the same basal solution together with taxol (Tx) in order to obtain a final concentration in the medium of 0.25 μm (0.25 Tx group), or of 0.5 μM (0.5 Tx group), or of 1 μM (1 Tx group), or of 5 μM (5 Tx group), or of 10 μM (10 Tx group).

The sham group was not subjected to the cold ischemia—reperfusion sequence.

The values correspond to means±SEM (n=32, performed as four different series of experiments over four weeks). ***: $p<0.001$.

As in the above model, the FIG. 2 data confirms that:

At certain concentrations, both cyclosporin A and taxol can increase the viability of cardiac cells during a cold ischemia—reperfusion sequence.

There exists an optimum concentration for each of these two agents around 1 μM (boxed results in FIG. 2), enabling cardiomyocyte viability to be increased by about 75% for cyclosporin A and about 90% for taxol ($p<0.001$).

2. Search for a CSA-TX Synergistic Effect 2.1 Equipment and methods

The cells and the procedures used were the same as in Part 1.

The St. Thomas solution used in this work have the following composition (in mM: $Na^+$: 147; $K^+$: 20; $Ca^{++}$: 2; $Mg^{++}$: 16; $Cl^-$: 203; $H_2O$: qsp 1000 milliliters (mL). Osmolarity: 388 mOsm/L.

The composition of the LYPS solution is given in Table 1 below.

TABLE 1

| Composition of the LYPS solution | |
|---|---|
| Components | LYPS |
| Ions | |
| $Na^+$ | 120 mM |
| $K^+$ | 13 mM |
| $Ca^{++}$ | 1 mM |
| $Mg^{++}$ | 4 mM |
| $Cl^-$ | 130 mM |
| Buffer | HEPES |
| Macromolecules | |
| PEG (PM 8000) | 2 g/L |
| PEG (PM 20,000) | 3 g/L |
| Metabolic substrates | |
| Glucose | 20 mM |
| Insulin | 250 IU/L |
| Glutamate | 1.4 mM |
| Aspartate | 2 mM |
| Pyruvate | 2.5 mM |
| Cardioprotective agents | |
| Cyclosporin | 1 μM |
| Taxol (paclitaxel) | 1 μM |
| Procaine | 1 mM |
| pH | 7.35 |
| Osmolarity (mOsm/L) | 290-310 |

The solution was prepared as follows:

The salts (NaCl, KCl, $CaCl_2$, $MgSO_4$) were weighed out and dissolved by stirring at ambient temperature in a known volume of water (about 700 mL in order to prepare one liter of final solution).

Adding HEPES, procaine hydrochloride, glucose, and sodium pyruvate under stirring.

Weighing out the following compounds independently: glutamic acid, aspartic acid, PEG 8000, and PEG 20,000, and dissolving them under stirring at a temperature of 40° C. in small volumes of water (about 25 mL in order to prepare 1 L of final solution).

Waiting for the above compounds to dissolve and adding them to the initial mixture, while still stirring.

Adding the last three compounds, insulin, cyclosporin A, and paclitaxel as previously dissolved in their vehicles under stirring and at ambient temperature.

Adjusting the volume to almost 1 L (950 mL in order to prepare 1 L of final solution).

Measuring the pH at 25° C.: it should be about 4.80.

Adjusting the pH to 7.15 using 10N NaOH at 25° C.

Filtering the solution at 0.22 micrometers (μm).

Placing the solution at 4° C.

Once the temperature has been lowered, verifying the pH at 4° C.: it should be about 7.40.

Pyruvate, glutamate, and aspartate were introduced respectively in the form of sodium pyruvate ($C_3H_3NaO_3$), glutamic acid ($C_5H_9NO_4$) and potassium aspartic acid ($C_4H_6NO_4$). The $Na^+$, $K^+$, $Ca^{++}$, and $Mg^{++}$ ions were introduced in the form of NaCl, KCl, $CaCl_2$, and $MgSO_4$ in order to obtain the desired total concentrations in the end.

2.2 Result. Cell Model of Cultured Rate Cardiac Cells

Figure 3:
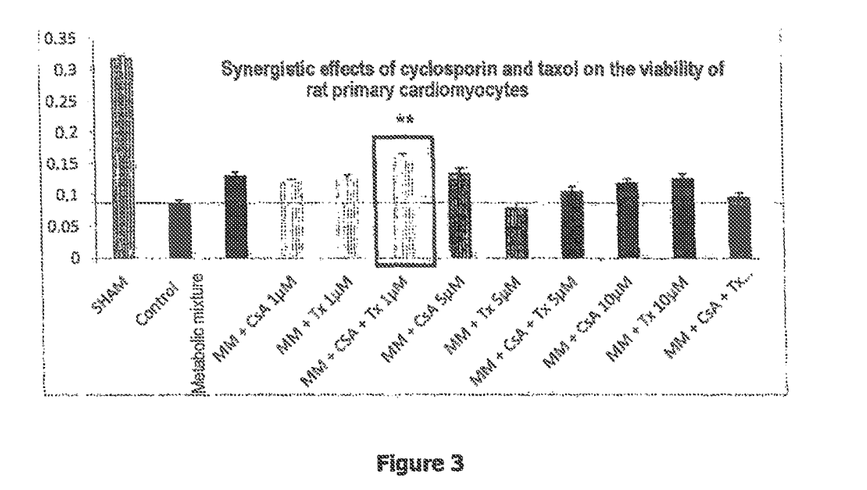
FIG. 3 shows the synergistic effect of cyclosporin and taxol on the viability of rat primary cardiomyocytes.

As above, the viability of primary cardiomyocytes was evaluated after 24 h of cold ischemia and 24 h of reperfusion. During the cold ischemia, the cells were maintained in various different media, and the corresponding results are shown in FIG. 3:

In a St. Thomas basal solution (cardioplegic solution)="control" group.

In the LYPS solution (without cyclosporin A and without taxol)=mixed "metabolic" or "MM" group.

In the same "MM" solution plus cyclosporin A (CsA) only, taxol (Tx) only, or a combination of CsA+Tx, with a final concentration in the medium of 1 µM for each of the two compounds.

The same combinations as above were prepared using concentrations of CsA and Tx of 5 µM and of 10 µM;

The sham group was not subjected to the cold ischemia—reperfusion sequence.

The values correspond to means±SEM (n=32, performed as four different series of experiments over four weeks). **: p<0.01.

The data in FIG. 3 shows that:

The mixed metabolic solution (MM=LYPS solution without CsA or Tx) protects cardiomyocytes better than the control situation (=St. Thomas solution).

Cyclosporin A and taxol, when added singly to LYPS adds nothing in terms of cardioprotective effect. Specifically, the "MM+CsA 1 µM", "MM+Tx 1 µM", "MM+CsA 5 µM"; "MM+Tx 5 µM"; "MM+CsA 10 µM", and "MM+Tx 10 µM" are identical or not as good as the "MM" reference group.

Only the CsA+Tx combination when added to LYPS at a concentration of 1 µm shows a marked cardioprotective effect, with cell viability being increased by 23% relative to the "MM" only LYPS group. The other combinations at 5 µM and at 10 µM add nothing, and appear to be somewhat deleterious.

2.3 Cell Model using H9c2 Cell Line Cardiac Cells

Figure 4:
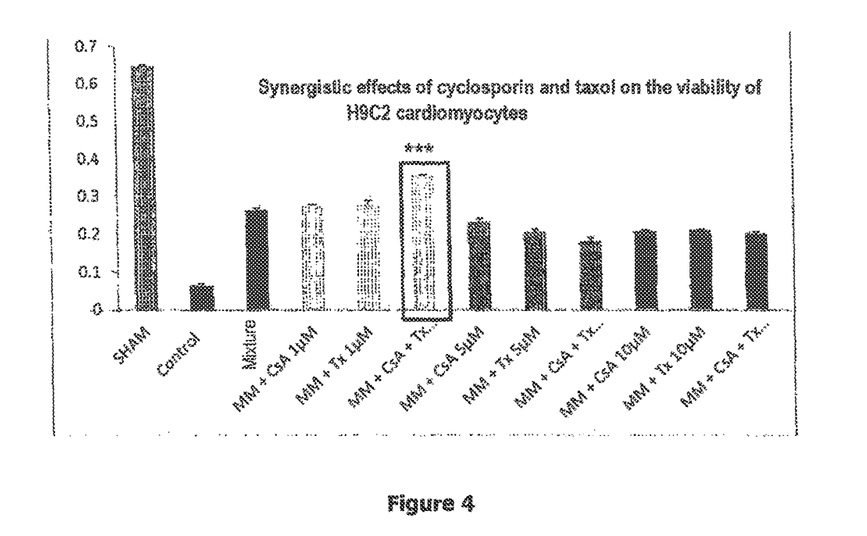
FIG. 4 shows the synergistic effect on cyclosporin and taxol on the viability of H9c2 cardiomyocytes.

As before, the viability of H9c2 cardiomyocytes was evaluated after 24 h cold ischemia and 24 h reperfusion. During the cold ischemia, the cells were maintained in various different media and the corresponding results are shown in FIG. 4:

In a St. Thomas basal solution (cardioplegic solution)="control" group.

In the LYPS solution (without cyclosporin A and without taxol)=mixed "metabolic" or "MM" group.

In the same "MM" solution plus cyclosporin A (CsA) only, taxol (Tx) only, or a combination of CsA+Tx, with a final concentration in the medium of 1 µM for each of the two compounds.

The same combinations as above were prepared suing concentrations of CsA and Tx of 5 µM and of 10 µM;

The sham group was not subjected to the cold ischemia—reperfusion sequence.

The values correspond to means±SEM (n=32, performed as four different series of experiments over four weeks). ***: p<0.001.

The data of FIG. 4 confirms that:

The mixed metabolic solution (MM=LYPS solution without CsA or Tx) protects cardiomyocytes better than the control situation (=St. Thomas solution, black bar).

Cyclosporin A and taxol, when added singly to LYPS adds nothing in terms of cardioprotective effect.

Specifically, the "MM+CsA 1 µM", "MM+Tx 1 µM", "MM+CsA 5 µM"; "MM+Tx 5 µM"; "MM+CsA 10 µM", and "MM+Tx 10 µM" are identical or not as good as the "MM" reference group.

Only the CsA+Tx combination when added to LYPS at a concentration of 1 µm shows a marked cardioprotective effect, with cell viability being increased by 34% relative to the "MM" only LYPS group. The other combinations at 5 µM and at 10 µM add nothing, and appear to be somewhat deleterious.

3. Confirming a CSA-TX Synergistic Effect on Whole Heart

In order to confirm the synergistic cardioprotective effect of the "cyclosporin A-taxol" association, studies were performed on an isolated whole rat heart model subjected to a cold ischemia—reperfusion sequence. In order to come closer still to the conditions that are encountered clinically, the Celsior solution was used, which solution is known to surgeons and is capable of providing good initial protection against ischemia—reperfusion lesions. Taxol, or cyclosporin, or the combination of both of those agents, were tested at the concentration of 1 µM, as recommended by the above work.

The Celsior solution is an aqueous solution containing 100 mM of $Na^+$, 15 mM of $K^+$, 0.25 mM of $Ca^{++}$, 41.5 mM of $Cl^-$, 13 mM of $Mg^{++}$, 80 mM of lactobionate, 60 mM of mannitol, 20 mM of glutamate, 30 mM of histidine, and 3 mM of reduced glutathion.

3.1 Equipment and Methods 3.1.1 Extracting Hearts and Cold Ischemia

The rats were anesthetized by intraperitoneal injection of sodium pentobarbital (50 milligrams per kilogram (mg/kg)). They were then placed in dorsal decubitus. After isolating the femoral vein, heparin was administered intravenously (200 IU/kg). An abdominal incision was made, followed by a thoracic incision. The sternum was pulled towards the rat's head, using a clamp, and the diaphragm was dissected. The heart isolated from its pericardium was excised and stopped in the hypothermic Celsior solution. The heart was then perfused for 3 minutes (min) using the same solution optionally having cyclosporin A, taxol, or the combination of both agents added thereto, at a concentration of 1 µM in the final solution. The hearts were then placed at 4° C. in the same solution for 8 h (the cold ischemia stage), prior to reperfusion (the reanimation stage).

3.1.2 Reperfusion of the Hearts and Functional Evaluation

After 8 h of cold ischemia, each heart was fastened by its aorta to a cannula for continuous retrograde perfusion using Krebs Henseleit (KH, having the following composition in mM: glucose 11.0; NaCl 118.5: KCl 4.75; $MgSO_4$ 1.19, $KH_2PO_4$ 1.2; $NaHCO_3$ 24.0; $CaCl_2$ 1.4). A constant pressure of 100 centimeters (cm) of $H_2O$ (corresponding to 74 millimeters of mercury (mmHg)) was imposed. The KH solution was bubbled continuously with 95% $O_2$+5% $CO_2$, in order to maintain its pH at 7.4. This perfusion technique is known to the person skilled in the art and known as the Langendorff mode perfusion system, or non-working beating heart.

A latex balloon was installed in the left ventricle and connected to a pressure sensor previously calibrated by internal calibration (0 to 200 mmHg). At the beginning of reperfusion, the balloon was inflated in order to obtain a telediastolic pressure of about 5 mmHg. Stimulation electrodes were then installed on the atria. The hearts were stimulated at a frequency of 300 beats per minute.

A recording system, made up of a pressure sensor, a monitor (HP 785334 A) and data acquisition software (Chart) served to measure the functional parameters at various times, including left ventricular developed pressure (LVDevP) and heart rate (HR).

3.1.3 Evaluation of Myocardiac Necrosis

At end of reperfusion, the heart was cut parallel to its base in five slices each having a thickness of about 2 mm. The slices were then incubated for 20 min at 37° C. in a 1% triphenyltetrazolium chloride (TTC) solution at pH 7.4. "Viable" myocardium appeared with a brick red color whereas the area of necrosis (AN) or infarcted zone appeared pale because it was not marked. The entire surface of the myocardium was considered as an area at risk (AR). For each slice, the ratio AN/AR was expressed as a percentage, representing the size of the infarctus. The sum of the infarctuses in all of the sections belonging to the same left ventricle gave the quantity of necrosis for the heart in question.

The lactate dehydrogenases (LDH) and the certain phospho-kinases (CPK) were collected from the coronary effluents of the rat hearts perfused in vitro. These enzymes are indicative of myocardiac necrosis. Their presence in the effluent is proportional to the level of myocardiac necrosis.

In practice, the rate of consumption of NADH was determined by photometry (at 340 nm), and it is proportional to the activity of the enzymes in the sample. The results are expressed in IU/L/g heart dry weight.

The statistical analysis consisted in comparing means (ANOVA), followed by the Bonferroni post-hoc test.

3.2 Protocol on a Perfused Isolated Heart Model

The purpose of this protocol was to come close to the conditions encountered by a cardiac graft in a clinical situation. It was thus decided to work on an isolated heart model placed in cold ischemia—reperfusion. The purpose of this study was thus to confirm the potential cardioprotective and synergistic effect of cyclosporin associated with taxol.

The protocol used studied the effects of these two agents on the functional restarting and on the necrosis of hearts that had been subjected to 8 h of cold ischemia at 4° C. followed by 1 h of reperfusion at 37° C. in Langendorff mode. Four groups of six hearts were randomized as follows:

A "control" group where the hearts were preserved for 8 h under cold ischemia in the Celsior solution.

A "Tx" group where the hearts were preserved for 8 h under cold ischemia in the Celsior solution plus taxol at 1 µM.

A "CsA" group where the hearts were preserved for 8 h under cold ischemia in the Celsior solution plus cyclosporin at 1 µM.

A "Tx+CsA" group where the hearts were preserved for 8 h under cold ischemia in the Celsior solution plus taxol and cyclosporin, both at 1 µM.

3.3 Functional Results

Figure 5:
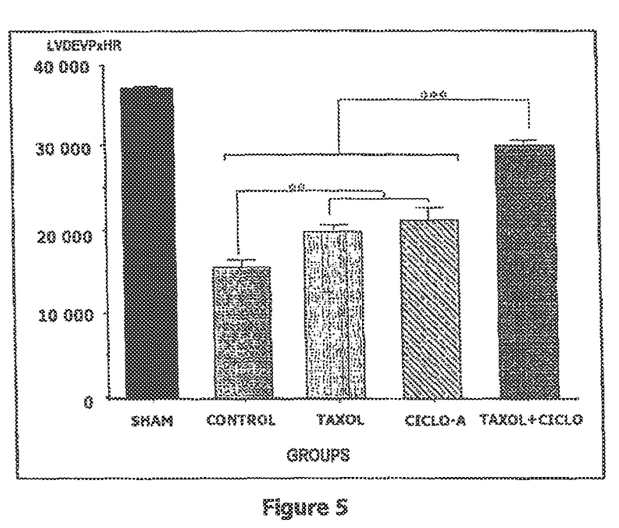
FIG. 5 shows the synergistic effect of cyclosporin and taxol on rat whole hearts following cold ischemia—reperfusion.

FIG. 5 shows the results obtained on hearts that have been preserved for 8 h at 4° C. in the Celsior solution ("control" group), plus 1 µM of taxol ("taxol" group), or plus 1 µM of cyclosporin A ("cyclo-A" group), or plus 1 µM of cyclosporin A and 1 µM of taxol ("taxol+cyclo") group. The "sham" group was a non-ischemic control group. At the end of cold ischemia, the hearts were reperfused for 1 h and functional evaluations were undertaken: the index LVDevP× HR corresponds to the left ventricular developed pressure (LVDevP) multiplied by the heart rate (HR). The data comprises means on six hearts±SEM. : $p<0.01$; *: $p<0.001$.

The data in FIG. 5 confirms that:

Taxol on its own, like cyclosporin A on its own, at 1 µM improves the restarting of hearts on reperfusion. Specifically, an improvement of 25% in LVDevPXHR is observed compared with the control group ($p<0.01$).

Taxol associated with cyclosporin A gives rise to major protection of the heart on reperfusion. Thus, function is improved by 50% to 80% compared with the other groups that had been preserved ($p<0.001$).

Since both cyclosporin and taxol were used at their concentration of maximum effectiveness (1 µM), only a synergistic action of the two agents can explain such a large observed improvement.

3.4 Results Relative to Necrosis

Figure 6:
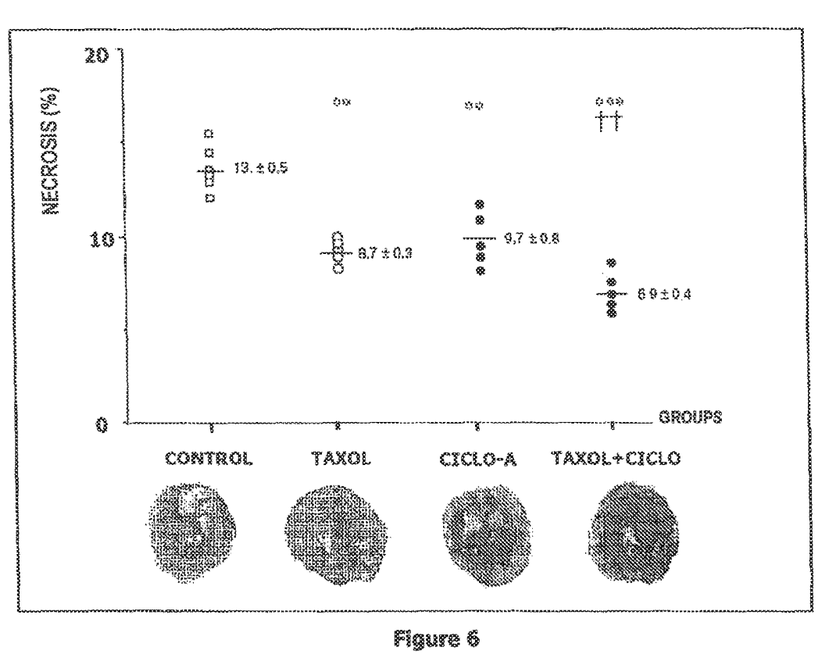
FIG. 6 shows the synergistic effect of cyclosporin and taxol on rat whole heart necrosis on reperfusion.

The heats were preserved for 8 h at 4° C. in the Celsior solution ("control" group), plus 1 µM of taxol ("taxol" group), or plus 1 µM of cyclosporin A ("cyclo" group), or plus 1 µM of cyclosporin A and 1 µM of taxol ("Tx+cyclo") group. At the end of cold ischemia, the hearts were reperfused and the size of infarctus was analyzed histologically after using TTC dye. The results obtained are shown in FIG. 6, where the data are means over six hearts±SEM. : $p<0.01$; *: $p<0.001$ (relative to the control group).

By histological measurement of the size of infarctus, the data of FIG. 6 likewise confirms that taxol associated with cyclosporin A gives rise to maximum protection in which infarctus drops to 6.9% of the zone at risk (compared with 8.7% and 9.7% respectively for Tx and CsA on their own), which corresponds to a reduction of 47% relative to the control group ($p<0.001$).

4. Conclusions

The studies that have been performed reveal the impact of the combined use of Cyclosporin A and Taxol on the viability of a heart when subjected to a cold ischemia—reperfusion sequence, a sequence that is to be found in human surgery when preserving cardiac grafts.

The conclusions are as follows:

In the Cell Models:

Both cyclosporin A and taxol at certain concentrations increase the viability of cardiac cells during a cold ischemia—reperfusion sequence.

Each of these two agents has an optimum concentration around 1 µm, enabling the viability of cardiomyocytes to be increased in the range 25% to 75% for cyclosporin A and in the range 25% to 90% for taxol, depending on the cell model used.

Cyclosporin A and taxol, when added on their own to the LYPS solution provide nothing in terms of cardioprotective effect. In contrast, the combination of CsA+Tx, added to the LYPS solution at a concentration of 1 µM shows a marked cardioprotective effect, with an increased cell viability lying in the range 23% to 34%, depending on the cell model used. It should be observed that the other combinations of 5 µM and 10 µM add nothing and indeed appear to be somewhat deleterious, further supporting the idea of an optimum concentration. These results, obtained on two different cell models for cultured cardiomyocytes, support the idea of synergistic action between the two compounds, since the observed anti-ischemia effectiveness results only from the condition that both compounds be present at their optimum concentrations.

In the Isolated Heart Model:

Taxol associated with cyclosporin A in the Celsior solution also leads to major protection of hearts on reperfusion (function improved by 80%, necrosis diminished by 47%).

Since cyclosporin and taxol were used at their concentration of maximum effectiveness (1 μM), only a synergistic action between the two agents can explain such a large observed improvement.

The invention claimed is:

1. A solution for organ preservation, the solution comprising:
    100 mM to 130 mM of $Na^+$;
    12 mM to 15 mM of $K^+$;
    0.25 mM to 1.3 mM of $Ca^{++}$;
    0.5 μM to 1.5 μM of cyclosporin A; and
    0.5 μM to 1.5 μM of taxol;
    wherein cyclosporin A and taxol act synergistically, and provide an anti-ischemic action.

2. The solution according to claim 1, comprising:
    110 to 130 mM of $Na^+$;
    12 to 14 mM of $K^+$; and
    0.7 to 1.3 mM of $Ca^{++}$.

3. The solution according to claim 1, further comprising magnesium $Mg^{++}$.

4. The solution according to claim 1, further comprising:
    polyethylene glycol having a mean molecular weight of 7200 to 8800 daltons; and
    polyethylene glycol having a mean molecular weight of 18,000 to 22,000 daltons.

5. The solution according to claim 1, further comprising insulin and glucose.

6. The solution according to claim 1, further comprising insulin and pyruvate.

7. The solution according to claim 1, further comprising pyruvate, aspartate, and glutamate.

8. The solution according to claim 1, further comprising procaine.

9. The solution according to claim 1, further comprising adenosine.

10. The solution according to claim 1, further comprising reduced glutathione.

11. The solution according to claim 1, comprising:
    110 to 130 mM of $Na^+$;
    12 to 14 mM of $K^+$;
    0.7 to 1.3 mM of $Ca^{++}$;
    0.5 to 1.5 μM of cyclosporin A;
    0.5 to 1.5 μM of taxol;
    3.5 to 4.5 mM of $Mg^{++}$;
    118 to 142 mM of $Cl^-$;
    1.5 to 2.5 g/L of polyethylene glycol having a mean molecular weight of 7200 to 8800 daltons;
    2 to 4 g/L of polyethylene glycol having a mean molecular weight of 18,000 to 22,000 daltons;
    240 to 260 IU/L of insulin;
    19 to 21 mM of glucose;
    2.4 to 2.6 mM of pyruvate;
    1 to 3 mM of aspartate;
    0.4 to 2.4 mM of glutamate;
    0.5 to 1.5 mM of procaine; and
    water.

12. The solution according to claim 1, comprising 0.7 to 1.3 μM of taxol and 0.7 to 1.3 μM of cyclosporin A.

13. The solution according to claim 1, comprising:
    120 mM of $Na^+$;
    13 mM of $K^+$;
    1 mM of $Ca^{++}$;
    1 μM of cyclosporin A;
    1 μM of taxol;
    4 mM of $Mg^{++}$;
    130 mM of $Cl^-$;
    2 g/L of polyethylene glycol having a mean molecular weight of 7200 to 8800 daltons;
    3 g/L of polyethylene glycol having a mean molecular weight of 18,000 to 22,000 daltons;
    250 IU/L of insulin;
    20 mM of glucose;
    2.5 mM of pyruvate;
    2 mM of aspartate;
    1.4 mM of glutamate;
    1 mM of procaine; and
    water.

14. The solution according to claim 1, wherein the solution has an osmolarity in a range of from 280 mOsm/L to 320 mOsm/L.

15. The solution according to claim 1, wherein the solution is buffered to a pH of 7.3 to 7.4.

16. The solution according to claim 15, wherein the solution is buffered with HEPES solution.

17. The solution according to claim 1, further comprising a compound for increasing membrane fluidity.

* * * * *